United States Patent [19]
Nerenberg

[11] 3,930,973
[45] Jan. 6, 1976

[54] ELECTROPHORETIC PROCESS

[76] Inventor: Samuel T. Nerenberg, 2906 Washington, Wilmette, Ill. 60091

[22] Filed: Nov. 15, 1972

[21] Appl. No.: 306,714

Related U.S. Application Data

[63] Continuation-in-part of Ser. No. 233,448, March 10, 1972, abandoned.

[52] U.S. Cl............ 204/180 S; 204/180 S; 204/299
[51] Int. Cl.² ........................................ B01D 13/02
[58] Field of Search ............ 204/299, 180 S, 180 G

[56] References Cited
UNITED STATES PATENTS

| | | | |
|---|---|---|---|
| 2,147,458 | 2/1939 | Rohland............................. | 91/62.5 |
| 2,843,540 | 7/1958 | Ressler ............................ | 204/180 S |
| 2,962,425 | 11/1960 | Sharpsteen, Jr. et al..... | 204/180 S X |
| 2,962,426 | 11/1960 | Sharpsteen, Jr. ............ | 204/180 S X |
| 3,317,417 | 5/1967 | Raymond........................ | 204/299 |
| 3,317,418 | 5/1967 | Zec.................................. | 204/299 |
| 3,378,481 | 4/1968 | Saravis et al...................... | 204/299 |
| 3,402,118 | 9/1968 | Mutter............................. | 204/299 |
| 3,407,133 | 10/1968 | Oliva et al. ..................... | 204/299 |
| 3,421,998 | 1/1969 | Yallen............................. | 204/299 |
| 3,432,414 | 3/1969 | Rand............................... | 204/180 G |
| 3,432,424 | 3/1969 | Zec................................... | 204/299 |
| 3,594,263 | 7/1971 | Dwyer et al. ................... | 204/180 S |
| 3,616,387 | 10/1971 | Siebert et al................... | 204/180 G |
| 3,715,295 | 2/1973 | Tocci............:................... | 204/180 G |

OTHER PUBLICATIONS

Heftmann, "Chromatography," 2nd Ed., pp. 255-259, 269 and 270.

Canley, "Electrophoresis and Immunoelectrophoresis," pp. 1, and 230-233, Little, Brown & Co., Boston, 1969.

Primary Examiner—John H. Mack
Assistant Examiner—A. C. Prescott

[57] ABSTRACT

A method and apparatus for electrophoresis, counter electrophoresis, or immuno electrophoresis on a cellulose acetate membrane carried out on a flat rigid support plate supported over buffer reservoirs of opposite polarity. The membrane is wetted with buffer solution and pressed against the plate to flatten it and excess buffer solution is removed. Wicks are placed at opposite edges of the membrane and extend into the buffer reservoirs. Multiple samples are applied to the membrane and are electrophoresed. Several membranes may be placed across the plate with interconnecting wicks for series electrophoresis. Or several membranes may be superposed on the plate with diffusion sample to the lowermost plate for parallel electrophoresis.

The invention also provides a system for rapid and accurate placement of samples to be tested on the membrane.

The method and apparatus in another embodiment are suitable for thin layer gel chromatography and electrophoresis.

4 Claims, 7 Drawing Figures

ELECTROPHORETIC PROCESS

CROSS-REFERENCE TO RELATED APPLICATION

This application is a continuation-in-part of my co-pending application Ser. No. 233,448, filed Mar. 10, 1972 now abandoned.

BACKGROUND OF THE INVENTION

The fractionation of macromolecules by electrophoresis on various supporting media has been carried out in clinical laboratories for a number of years as for screening the blood serum of hospital patients. A cellulose acetate membrane support medium has been recognized as possessing many advantages over filter paper and gels. An apparatus and technique for agar electrophoresis on a plate is described in the article, Nerenberg, S. T. et al., "Laboratory Diagnosis of Specific Organ Diseases By Means of Combined Serum Isoenzyme Patterns," Amer. J. Clin. Pathol. 51:429, 1969. A membrane suspension technique is employed for electrophoresis on cellulose acetate, commonly by means of a so-called "Microzone Cell" sold by Beckman Instruments. It comprises a frame with spring loaded plastic keys which fit into a series of holes punched into opposite borders of the membrane to pull it taut. The membrane portions to the outside of the holes are placed into contact with elongated facing buffer chambers. This elaborate technique was considered necessary to carry out electrophoresis without short circuiting through buffer solution.

The above system has a number of disadvantages. It has been found that approximately half of the relatively expensive cellulose acetate membrane cannot be utilized because of the perforations used for suspension. Also, the lack of rigidity of the suspended membranes renders it difficult to apply a large number of samples at each application. Also different samples requiring different buffers, such as serum and urine, may not be run at one time. In addition, the equipment is relatively expensive and a large amount of technician's time is necessary. Furthermore, the equipment requires the sample to be electrophoresed in the long axis of the membrane which is normally at least three or four times longer than it is wide which results in relatively few samples which can be applied to each membrane. Finally, it is difficult to suspend relatively large fragile sheets of the material to increase the number of samples applied.

SUMMARY OF INVENTION AND OBJECTS

It is a general object of the invention to provide an electrophoresis system for the fractionation of macromolecules such as proteins on a thin membrane, such as cellulose acetate, carried out on a solid support plate to overcome the aforementioned disadvantages of prior art apparatus and methods.

It is a particular object of the invention to increase the number of samples which may be economically electrophoresed in a single run as for screening the blood serum of hospital patients.

It is another object of the invention to provide a technique for simultaneously electrophoresing a plurality of membranes in series with the same or different buffer systems in each membrane.

It is a further object of the invention to provide a technique for simultaneously electrophoresing multiple samples which may be of different types on a plurality of superposed membranes run in parallel.

It is a still further object to provide a system for counter electrophoresis and immuno electrophoresis of large numbers of samples.

It is a still further object to provide in another embodiment of the invention a system for thin layer gel chromatography and electrophoresis.

It is a still further object to provide a system for accurate placement of multiple samples to be subjected to electrophoresis.

Other and further objects of the invention will be apparent from the following description taken in conjunction with the appended drawings.

In accordance with the present invention, a paper-thin liquid permeable unbacked membrane, preferably cellulose acetate, containing an electrically conductive buffer solution, is layered onto a rigid flat electrically non-conductive support plate. The membrane is pressed against the plate to provide a generally planar configuration to the same and excess buffer solution is removed from the membrane, and from the contact area between the membrane and plate. Buffer solution-containing wicks are positioned to overlay the opposing edges of each membrane and to extend into containers of buffer solution.

Multiple samples are applied to the membrane surface by utilizing an applicator including mating spaced teeth which are contacted with different samples on mating spaced surfaces or platforms. The sample-containing teeth are then contacted with the exposed membrane surface for transfer of the same. Thereafter, the samples are electrophoretically fractionated by the passage of an electric current across the membrane with the buffer in the containers maintained at opposite polarities. Allso, counter electrophoresis and immuno electrophoresis may be performed with the aforementioned advantages.

As used herein, the term "electrophoresis" includes that portion of an immuno electrophoresis or counter electrophoresis technique in which electric current is passed to separate components of the mixed macromolecular sample.

The aforementioned general technique of solid support electrophoresis across a cellulose acetate membrane on a rigid support plate is predicated upon the discovery that excess buffer solution may be removed to an extent that electric current passes through the membrane rather than being short-circuited through a complete path of buffer solution.

Elimination of the wasteful membrane perforations, necessary for the suspension system, enables multiple samples to be electrophoresed in the short dimension of an elongated cellulose acetate membrane. Furthermore, the accuracy of application against a rigid backing plate permits the samples to be applied relatively close together yielding a large number of samples per sheet.

Two, three, or more membranes may be layered in spacedapart relationship with interconnecting wicks containing buffer solutions for electrophoresis in series with the same or different buffer solutions in each membrane. In another technique, a number of membranes may be superimposed with the application of a series of samples to the outermost one. These samples rapidly diffuse through the membranes so that electrophoresis is carried out simultaneously in parallel in all membranes. In this manner, the same sample may be analyzed for different components after a single run. In another technique, cellulose acetate membranes may be layered onto both sides of the support plate as, after pressing, the membranes are strongly adherent to the plate. Thereafter, buffer solution-containing wicks may be provided for each membrane so that electrophoresis may be run simultaneously.

DETAILED DESCRIPTION OF THE PREFERRED EMBODIMENTS

Figure 1:
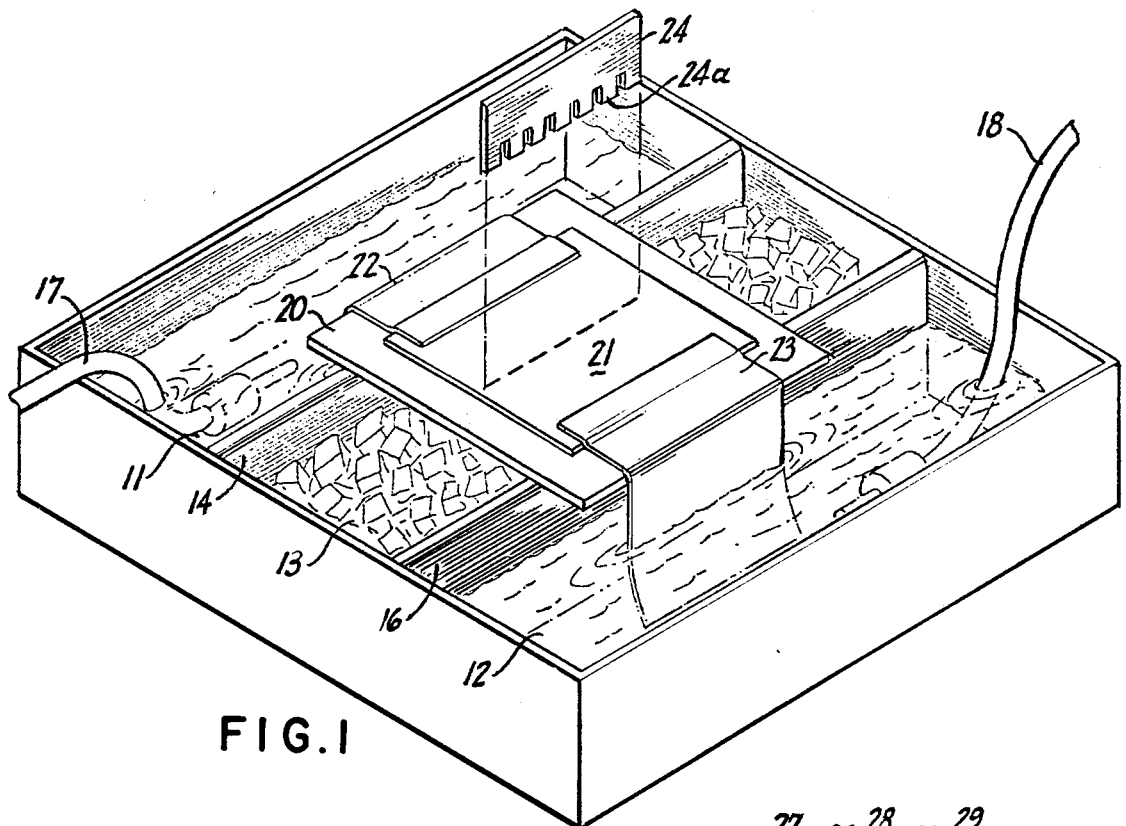
FIG. 1 is a view in perspective of one apparatus for carrying out membrane electrophoresis on a solid support.

Referring to FIG. 1, an electrophoresis assembly is illustrated in accordance with the present invention. It includes anode and cathode buffer chambers 11 and 12, respectively, with a centrally disposed container 13 for coolant such as ice to prevent the plate from heating up during passage of electrical current. In the illustrated device, partition 14 provides a common wall between buffer chamber 11 and cooling chamber 13 and, similarly, partition 16 provides a common wall between buffer chamber 12 and chamber 13. Removable electrodes 17 and 18 are provided in chambers 11 and 12, respectively. The electrodes are maintained at opposite polarities during electrophoresis to supply the current.

An essentially rigid generally flat support plate 20 formed of an electrically non-conductive material such as glass is illustrated as being supported by resting upon the top edges of partitions 14 and 16.

A cellulose acetate membrane 21 is layered onto plate 20 in the manner to be described hereinafter. These strips are suitably of a size (a) sold by Gelman Instruments Co. under the name "Sepraphore III," size 5.7 × 14.6 cm, or (b) sold by Schleicher & Schuell (2.5 × 30 cm or 5 × 20 cm). Paths of buffer solution are provided by a pair of wicks 22 and 23 suitably of a sorbent material such as paper toweling such as sold under the name "Selfold Towels" by Fort Howard Paper Company. These wicks layered onto plate 20 to overlap opposing edges of membrane 21 and extend into the buffer solution contained in chambers 11 and 12, respectively.

An applicator 24 including teeth 24a is suitable for application of a number of samples to membrane 21, as described hereinafter. One type of multi-sample applicator, made of stainless steel, is described in the publication, Kohn, J. "A Multi-Sample Applicator For Zone Electrophoresis." *Clin. Chim. Acta* 18:65, 1967. The sample adsorbing surface is grooved to pick up a relatively small quantity of sample.

Another type of applicator formed of plastic is a modification of a so-called Cordis applicator. These applicators made of plastic are modified by removal of segments of plastic to form the spacing for the teeth in the applicator. A greater volume of sample may be applied per unit length with this latter type of applicator.

Figure 7:
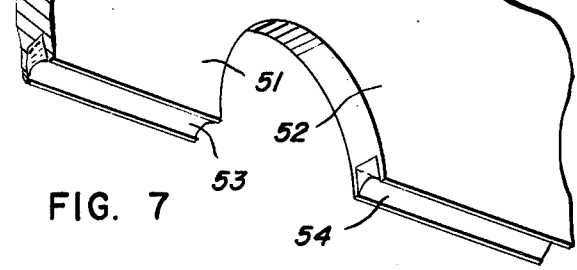
FIG. 7 is an enlarged perspective broken view showing a portion of the underside of the sample applicator.

A suitable applicator structure is shown on an enlarged scale in FIG. 7 in which 51 and 52 represent successive teeth having grooves 53 and 54, respectively, to hold the small quantities of sample being transferred.

Before layering samples onto membrane 21, a coolant such as ice is placed in cooling chamber 13 in preparation for applying current to electrodes 17 and 18. The system is then equilibrated for, say, 5 minutes with current passage.

After equilibration, membrane 21 is wetted from below in a buffer solution of the desired pH value (normally alkaline) and placed on plate 20. Wicks 22 and 23 are cut from paper towels, wetted with buffer solution, and are positioned so that about 1 cm of one edge of each wick overlaps opposing edges of the membranes. The other edges of the wicks extend into the buffer solution in chambers 11 and 12, respectively. In order to remove excess buffer solution from the membrane, the contact area between the membrane and plate, and the overlapping wick portions, paper toweling may be placed over the membrane and common wick area and pressed firmly against plate 20 as with a photographic roller. This not only forces out excess buffer solution which would otherwise short-circuit during electrophoresis but also causes the membrane to be flattened and to intimately contact the plate 20. The paper towels used for buffer adsorption are then discarded and the procedure may be repeated, if necessary, for removing any remaining surface fluid.

Thereafter, sample is applied to the center of the membrane as illustrated in FIG. 1. A convenient technique for loading multiple samples onto the teeth of applicator 24 utilizes a sample holder containing individual surfaces or platforms, each containing a small quantity (e.g., one drop) of specimen. The platforms and applicator teeth are spaced to be in registry. The applicator teeth are contacted with and adsorb sample for transfer to the membrane by contacting the same for, say, 15 seconds.

Figure 6:
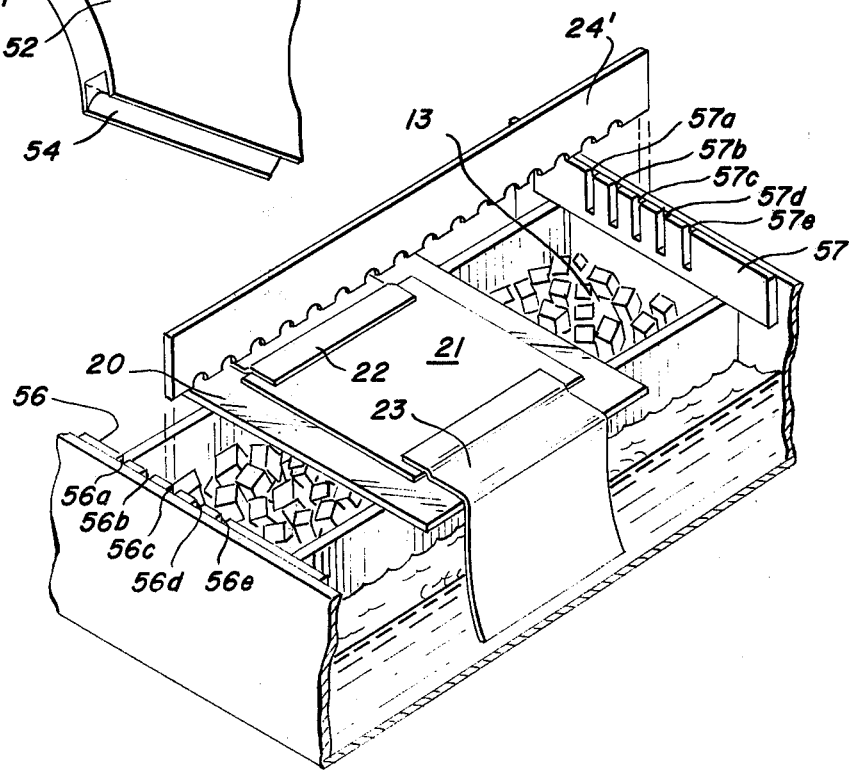
FIG. 6 is a view in perspective of a broken portion of an apparatus generally similar to that of FIG. 1, but showing the guidance system for the sample applicator.

After the applicator has taken up the samples in the grooves of its teeth, it is positioned for deposit of its samples at the precise locations desired in the manner shown in FIG. 6. Brackets 56 and 57, located on the interior of the end walls of chamber 13, contain grooves 56a through 56e, and grooves 57a through 57e, respectively; and one end of applicator 24' can be set into a groove in bracket 56 while the other end is set into a groove in bracket 57 to provide firm guidance for the applicator as it is moved downwardly into contact with the membrane to deposit its samples thereon. The applicator is then held firmly in position for a few seconds to assure proper deposit of its samples, movement during the deposit being precluded by the guidance of the grooves and by the rigidity of the supported membrane. Should there be failure to transfer one or more samples, or an inadequate transfer of samples, the applicator may once more be brought into contact with the samples and then returned to contact with the membrane with assurance that each tooth of the applicator will return to the same location on the membrane as its first contact therewith.

For transfer of samples to the mid-line of the membrane, grooves 56c and 57c will be used. For transfer of samples to other positions or where more than one line of samples is to be used, other pairs of grooves may be used.

After sample application, electrophoresis is performed by applying a current (e.g., 250 volts and 15–20 mA) for, say, 20–30 minutes.

Figure 4:
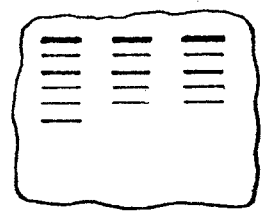
FIG. 4 is an expanded portion of a membrane illustrating multiple electrophoretically fractionated samples.

After completion of electrophoresis the membranes are removed from the glass plate and stained for the desired constituents. For a blood serum sample some of the constituents which may be demonstrated by electrophoresis include isoenzymes, lipoproteins, glycoproteins, hemoglobin variants, and haptoglobins. FIG. 4 illustrates a magnified portion of a typical membrane after electrophoresis and staining. The stained membranes may be removed from the glass plate and placed on a suitable backing such as Cronar film sold by DuPont, cleared in a mixture of say, acetic acid-methanol, and placed in a notebook.

Different stains are suitable for different components. For example, a suitable stain for protein is Ponceau Red S in a concentration of 2 grams/liter in a solution of trichloroacetic acid (75 grams/liter) and sulfosalicylic acid (75 grams/liter). Glycoproteins may be stained with PAS as described in Kohn, J., In Chromatographic and Electrophoretic Techniques. Ivor Smith, 2d ed., *Interscience*, New York, N.Y., 1968, chapter 3, p. 84. An o-dianisidine method may be utilized for analyzing haptoglobins.

Figure 2:
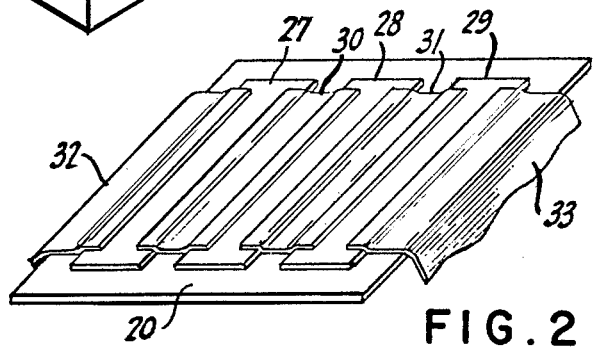
FIGS. 2 and 3 are different embodiments of electrophoresis on the plate of FIG. 1 carried out in series and parallel, respectively, in which the membrane thickness has been exaggerated for clarity.

Referring to FIG. 2, a number of membranes are illustrated in a relationship suitable for series electrophoresis on a single plate 20 utilizing the apparatus illustrated in FIG. 1. Three membranes 27, 28 and 29 are illustrated inter-connected by overlapping interconnecting wicks 30 and 31 and communicating with the buffer chambers, not shown, by wicks 32 and 33 of the same type as wicks 22 and 23 of FIG. 1. The same general technique as described above is utilized in this series configuration. Excess buffer solution is removed from membranes 27, 28 and 29, as well as interconnecting wicks 30 and 31.

Suitable positioning for sample application in a series oriented membrane as illustrated in FIG. 2 is as follows: on the cathodic membrane—an imaginary line joining the cathodic ⅓ of the strip with the anodic ⅔ of the same; on the middle membrane—in the middle, and on the anodic membrane on an imaginary line joining the cathodic ⅔ of the strip with the anodic ⅓. By the application of 14 specimens across each strip and utilizing both sides of the plate, as described hereinafter, as many as 84 specimens may be run simultaneously.

In the series arrangement of FIG. 2, the same buffer solutions may be employed in each membrane. However, an advantage of this series orientation is that buffer solutions at different pH values may be employed so that different components may be fractionated in each membrane simultaneously. For example, a TEB, tris (hydroxylmethyl) aminomethane-sodium ethylenediaminetetraacetate-borate (pH 9.1, 60 mol/liter) may be used for separation of hemoglobin variants and of serum haptoglobins while a barbital buffer (pH 8.6, 0.5 mol/liter) may be used for the remainder of the proteins. This arrangement is designated a discontinuous buffer system.

Figure 3:
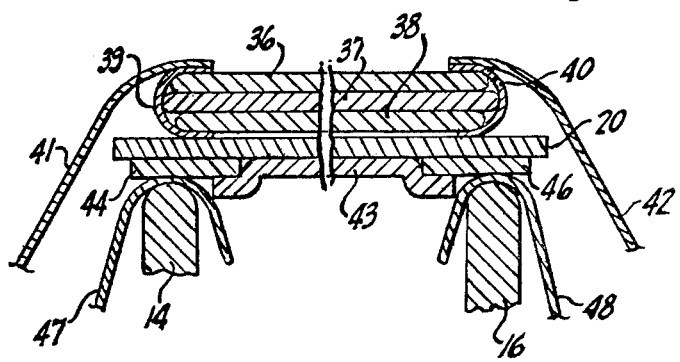

Referring to FIG. 3, an embodiment is illustrated utilizing a plate 20 and the general apparatus illustrated in FIG. 1, (a) for parallel electrophoretic runs, and (b) for utilizing both the upper and lower surface of the plate for simultaneous runs. The thicknesses of the plate, membranes, and wicks have been exaggerated for clarity.

Referring to the upper surface of plate 20, three wetted membranes 36, 37 and 38 are superposed one above the other and layered onto plate 20. Wetted wicks 39 and 40 are disposed at opposed outer edges of the membranes with the lower surface of each wick interposed between the plate 20 and membrane 38 and the upper surface of each wick folded over the opposed edges of the top surface of membrane 36 in an overlapping manner. Wicks 41 and 42 rest at their upper end upon the top surfaces of wicks 39 and 40, respectively, and at the lower end project into the buffer solutions of corresponding buffer reservoirs. Excess buffer solution is removed in the aforementioned manner and the system is equilibrated.

A plurality of samples are applied to the exposed surface of the outer membrane 36 with an applicator of the type illustrated in FIG. 1. Sufficient sample is deposited to diffuse through membranes 36 and 37 and onto membrane 38. Electrophoresis is then carried out in parallel by applying a current of, say, 400 volts and 15–20 mA for a time of about 45 minutes. In a single electrophoretic run each of the multiple samples is fractionated on all of the superposed membranes by parallel electrophoresis. Thereafter, the membranes are peeled off and a single sample may be stained in different manners on each membrane depending upon the desired component to be analyzed.

Referring again to FIG. 3, one technique is illustrated for layering the underside of plate 20 with a membrane 43 for simultaneous runs on both sides of the plate. Wick strips 44 and 46 are first layered along opposing sides of plate 20. Then membrane 43 is layered with its opposed edges overlapping the corresponding opposed wick strips. Excess buffer solution is removed as described above. This is facilitated because of the ready adherence of a wetted membrane to the glass plate. Wicks 47 and 48 are deposited to overlay corresponding partitions 14 and 16 with the lower wick portions projecting into opposed buffer reservoirs 11 and 12, respectively. Plate 20 is then supported on partitions 14 and 16 so that wicks 47 and 48 contact wick strips 44 and 46, respectively, to provide communication between opposed edges of membrane 46 and the buffer reservoirs. By application of an electric current to this system, electrophoresis may be performed simultaneously on both sides of the support plate.

Series and parallel orientations may be run on both sides of the plate to electrophorese a very large number of samples with a single run. By way of example, utilizing a 5 × 20 cm cellulose acetate strip, 23 specimens may be applied per membrane. A narrower size (e.g., 2.5 × 30 cm) membrane may be used for screening hemoglobin variants, haptoglobins, and hepatitis-associated antigen (Australia antigen) because the respective components migrate relatively short distances. In a typical run employing the series oriented membranes, protein fractions migrate about 2.5 cm in 20 minutes. Pathologic sera and variant-type hemoglobins were readily available by visual inspection.

The foregoing technique may also be employed for counter-electrophoresis, a form of electrophoresis used to detect a specific antigen by driving a protein sample (containing the antigen) against a monospecific antiserum for interaction with the formation of a precipitin line. This is feasible because the weakly charged immunoglobins flow along with the buffer in the reverse or retrograde direction compared to the antibodies. The technique may be employed for the detection of a variety of antigens at high sensitivity in a relatively short period of time (e.g., 45 minutes).

Briefly described, counter-electrophoresis according to the present invention includes applying a known control specimen from the teeth of an applicator to a membrane on a line of origin using an assembly as illustrated in FIG. 1. Then antiserum is applied from the applicator to the same membrane on a line at an angle with the origin. Electrophoresis is carried out at approximately 200V for 45 minutes. Thereafter the membrane is successively washed in saline solution and distilled water after which it is stained, as with Ponceau Red for 15 minutes and rinsed in 5% acetic acid solution to remove background stain. The area where the precipitin line is approximately midway between the origin line and antiserum application line is located and the distance is measured. This distance is used to apply antiserum parallel to the origin line for comparative analysis of known samples.

Among the advantages of carrying out counter-electrophoresis on cellulose acetate membranes as described above in comparison to using agar include (a) less antiserum is used, (b) the technique is more rapid (45 minutes compared to 2 hours), (c) the supporting medium is ready to use and the antiserum and antigen can be applied directly to the supporting medium without the need for producing wells (as required with agar), (d) a large number of samples (antigen) and antisera can be applied at one time with a multi-sample applicator on cellulose acetate in contrast to agar in which antigen and antisera wells must be filled individually. Finally, the distance between antigen and antiserum which is critical for accurate results, is dependent to a large extent on the titre of a given antiserum. Even relatively slight variation in the strength of an antiserum may lead to false negative findings due to a prozone phenomenon, i.e., excess antigen or antibody. Thus, the optimum distance between antigen and antiserum must be determined for each lot of antiserum. This distance is easier to determine with cellulose acetate than agar.

Another application of the electrophoresis technique described herein is for the electrophoretic portion of immuno electrophoresis. In this technique electrophoresis is first carried out upon multiple samples applied to a membrane in the foregoing manner. Thereafter multiple parallel lines of monospecific or multispecific antisera are interposed between the fractionated samples. After allowing sufficient diffusion time, the membrane is stained in the foregoing manner. For monospecific antiserum the formation of a precipitin line indicates the presence of the corresponding antigen in the sample. For a multispecific antiserum, the location of the precipitin line indicates the particular type of antigen present in the sample.

Figure 5:
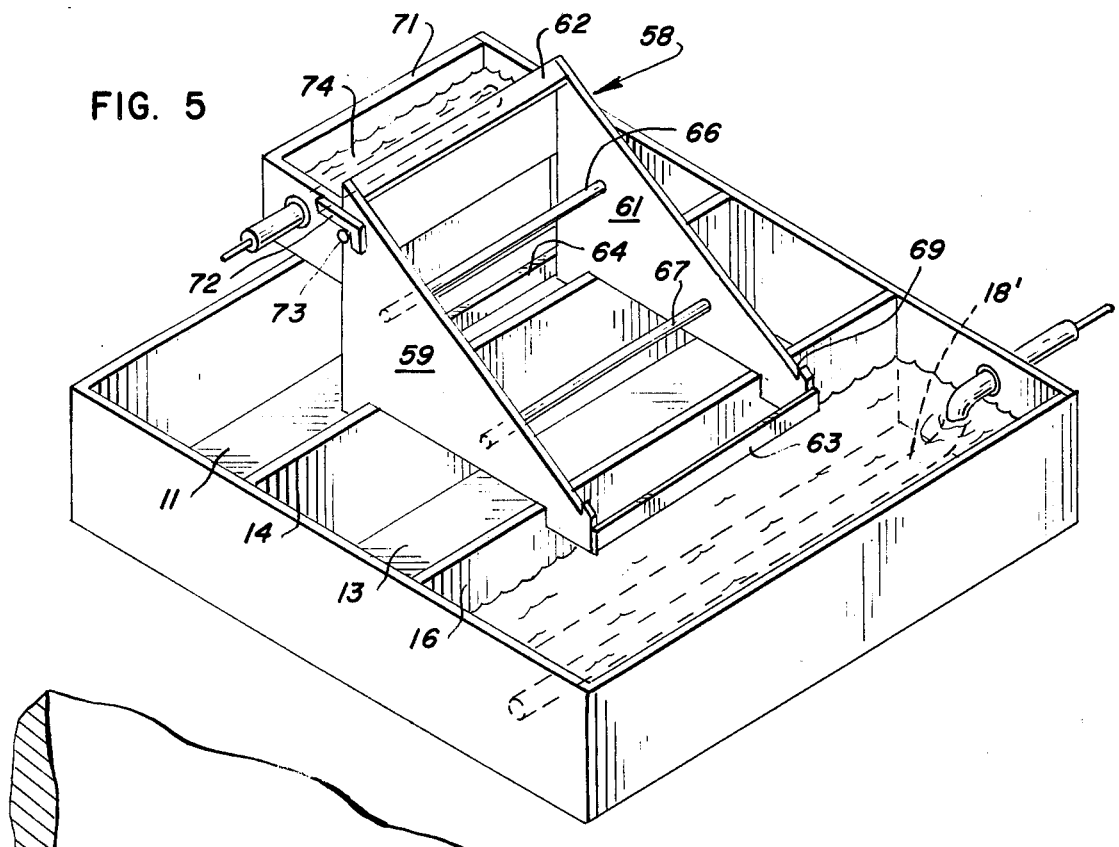
FIG. 5 is a view in perspective of a modification of the apparatus suitable for carrying out thin layer gel chromatography or thin layer gel electrophoresis.

FIG. 5 illustrates an embodiment of the invention adapted for thin layer gel electrophoresis or chromatography. In this system samples are separated into their molecular weight components while the samples are on a thin layer gel supported on a rigid plate at an angle to the horizontal, as for example an angle of 30°.

The embodiment of FIG. 5 utilizes partitions 14 and 16 of the apparatus of FIG. 1 as supports for holder 58. It does not require ice in chamber 13, nor buffer solution in chamber 11.

Holder 58 comprises essentially triangular side walls 59 and 61, suitably made of a rigid plastic material, held and braced together at the top by strip 62, at its narrow end by strip 63, at the bottom of its wide end by strip 64, and at intermediate points by rods 66 and 67. Side walls 59 and 61 are recessed at their bottom edges to prevent movement off the supporting partitions. The side walls also include notches 68 and 69 near the lower edges of their upper surfaces to provide support for the glass plate (not shown) on which the thin layer gel is supported.

Thin layer gel electrophoresis and chromatography require constant wetting of the thin gel layer, and for this purpose wicks (not shown) comparable to wicks 22 and 23 of FIG. 1 are provided, one wetted by the buffer solution in chamber 12, and the other wetted by buffer solution in auxiliary chamber 71 which is arranged to hang onto holder 58 by hooks 72 on the auxiliary chamber and pegs 73 on the side walls (only one hook and one peg being visible in FIG. 5).

Cathode 18' in cathode chamber 12 is similar to cathode 18 of FIG. 1, except that FIG. 6 illustrates a preferred embodiment in which the cathode lead passes through an end wall of chamber 12, and in which the cathode length is substantially the length of the chamber. Anode 74 in auxiliary chamber 71 is generally similar in structure to cathode 18', except that it is shorter because chamber 71 is shorter than chamber 12.

The cathode and anode are connected to the terminals of a source of direct current when the apparatus of FIG. 6 is used for thin gel electrophoresis. They are unconnected when the apparatus of FIG. 6 is used for thin gel chromatography.

It is apparent from the foregoing that the above system may be modified within the scope of the present invention so long as solid support is provided for the membrane which communicates with buffer solution without short-circuiting across the membrane.

As employed in the claims, electrophoresis includes that portion of immuno electrophoresis and counter-electrophoresis in which a sample is fractionated under the influence of an electric current.

I claim:
1. In an electrophoretic method for separating components of a mixed macromolecule sample, the steps of
   a. depositing an electrically conductive buffer solution containing at least two flexible paper-thin liquid-permeable membranes in spaced apart side-by-side relationship onto an essentially rigid generally flat support plate and layering an interconnecting buffer solution containing wick between adjacent edges of said membranes;
   b. pressing the membranes against the plate to provide a flat configuration to the membranes corresponding to that of the plate with intimate contact between the membranes and the plate;
   c. removing excess buffer solution from the membranes and area of contact between the membranes and the plate;
   d. providing two paths of buffer solution sorbed in wicks, each extending from an opposing edge of an outermost of said membranes to separate reservoirs of buffer solution;

e. applying a plurality of samples to the exposed surfaces of at least two of said membranes; and f. electrophesing the samples by passing an electric current across said membranes between said buffer reservoirs maintained at opposite polarities while said membranes are maintained having one surface in contact with said plate and with their opposite surfaces exposed.

2. A method as in claim 1 in which different buffers are layered for each membrane.

3. A method for carrying out counter-electrophoresis at an optimum distance to be maintained on a counter-electrophoresis membrane between an unknown protein sample and a plurality of antisera which comprises applying to a test membrane a plurality of site applications of a known control protein specimen along a first straight line perpendicular to the expected line of protein migration, applying to said membrane a plurality of site applications of a monospecific anti-serum for said protein along a second straight line spaced from said first straight line and at an angle thereto, subjecting said membrane to electrophoresis to cause at least a portion of said protein and at least a portion of said antiserum to migrate toward each other and form a precipitin line, measuring the distance between said first and second straight lines where the precipitin line is about midway between them and thereafter subjecting an unknown protein specimen to counter-electrophoresis on a test membrane on which the protein specimen is applied to said membrane in a plurality of site applications in a line perpendicular to the expected line of protein migration and a plurality of antisera are applied to said membrane in a plurality of site applications in a line parallel to said line of protein applications and spaced therefrom by said measured distance.

4. In an electrophoretic method for separating components of a mixed macromolecule sample, the steps of a. depositing an electrically conductive buffer solution containing a flexible paper-thin, liquid-permeable membrane onto opposite faces of an essentially rigid generally flat support plate;

b. pressing each membrane against the plate to provide a flat configuration to the membrane corresponding to that of the plate with intimate contact between the membrane and the plate;

c. removing excess buffer solution from each membrane and area of contact between the membrane and plate;

d. providing for each membrane two paths of buffer solution sorbed in wicks, each extending from an opposing edge of said membrane to separate reservoirs of buffer solution;

e. applying a plurality of samples to the exposed surface of each membrane; and f. simultaneously electrophesing the samples on each membrane by passing an electric current across said membrane between said buffer reservoirs maintained at opposite polarities while said membrane is maintained having one surface in contact with said plate and with its opposite surface exposed.

* * * * *